US012753447B2

(12) United States Patent
Park et al.

(10) Patent No.: US 12,753,447 B2
(45) Date of Patent: Oct. 6, 2026

(54) METHOD OF PREDICTING THERAPEUTIC RESPONSE AND PROGNOSIS OF METASTATIC BREAST CANCER TO CHEMOTHERAPEUTIC AGENTS, AND TREATING METASTATIC BREAST CANCER

(71) Applicant: Samsung Life Public Welfare Foundation, Seoul (KR)

(72) Inventors: Kyung Hee Park, Seoul (KR); Yeon Hee Park, Seoul (KR); Woong Yang Park, Seoul (KR); Ji Yeon Kim, Seoul (KR)

(73) Assignee: Samsung Life Public Welfare Foundation, Seoul (KR)

(*) Notice: Subject to any disclaimer, the term of this patent is extended or adjusted under 35 U.S.C. 154(b) by 708 days.

(21) Appl. No.: 18/077,907

(22) Filed: Dec. 8, 2022

(65) Prior Publication Data

US 2023/0235409 A1 Jul. 27, 2023

(30) Foreign Application Priority Data

Dec. 8, 2021 (KR) ........................ 10-2021-0175108

(51) Int. Cl.

| | |
|---|---|
| ***C12Q 1/6886*** | (2018.01) |
| ***A61K 31/337*** | (2006.01) |
| ***A61K 31/513*** | (2006.01) |
| ***A61K 31/519*** | (2006.01) |
| ***A61K 31/7068*** | (2006.01) |

(52) U.S. Cl.

CPC .......... *C12Q 1/6886* (2013.01); *A61K 31/337* (2013.01); *A61K 31/513* (2013.01); *A61K 31/519* (2013.01); *A61K 31/7068* (2013.01); *C12Q 2600/106* (2013.01); *C12Q 2600/156* (2013.01)

(58) Field of Classification Search

CPC ............ C12Q 1/6886; C12Q 2600/106; C12Q 2600/156

See application file for complete search history.

(56) References Cited

PUBLICATIONS

Kim, J-Y. et al. Breast Cancer Research and Treatment 178:367-377. Aug. 2019. (Year: 2019).*

Kim, J-Y. et al. Supplemental Table S1 of Breast Cancer Research and Treatment 178:367-377. Aug. 2019. (Year: 2019).*

Lang, G-T. et al. Nature Communications 11:5679 (doi.org/10.1038/s41467-020-19342-3). Nov. 2020. (Year: 2020).*

Rocca, A. et al. Therapeutic Advances in Medical Oncology 9(2):83-105. (Year: 2017).*

(Continued)

*Primary Examiner* — Diana B Johannsen

(74) *Attorney, Agent, or Firm* — Wood, Phillips, Katz, Clark & Mortimer

(57) ABSTRACT

The present disclosure relates to a method of predicting therapeutic response or prognosis of an anticancer drug for metastatic breast cancer, and treating HR+/HER2− metastatic breast cancer. When the biomarker of an embodiment of the present disclosure is used as a marker for predicting therapeutic response or prognosis of an anticancer drug for metastatic breast cancer of a specific type, it is possible to predict therapeutic response or prognosis of an anticancer drug, and accordingly, a therapeutic method suitable for a patient may be applied to maximize the treatment effect.

6 Claims, 2 Drawing Sheets

(56) References Cited

PUBLICATIONS

Oshi et al., "A Novel 4-gene Score to Predict Survival, Distant Metastasis and Response to Neoadjuvant Therapy in Breast Cancer", Cancers 2020, 12, 1148; doi:10.3390/cancers12051148.

Stravodimou et al., "The Future of ER+/HER2—Metastatic Breast Cancer Therapy: Beyond PI3K Inhibitors", AntiCancer Research 40: 4829-4841 (2020).

* cited by examiner

【FIGURE 1】
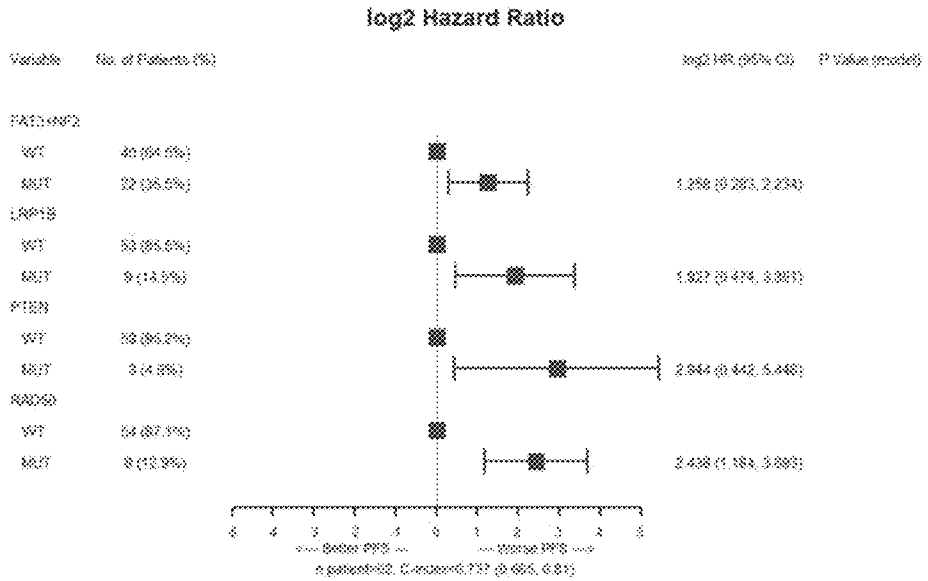
【FIGURE 2】
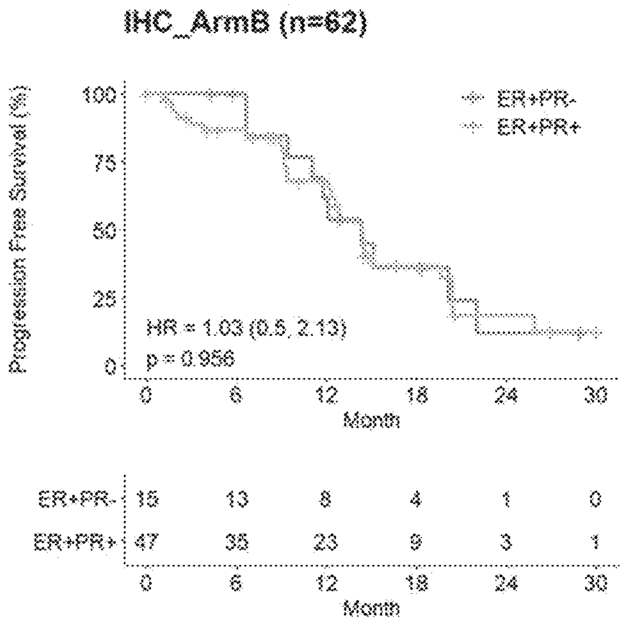

【FIGURE 3】
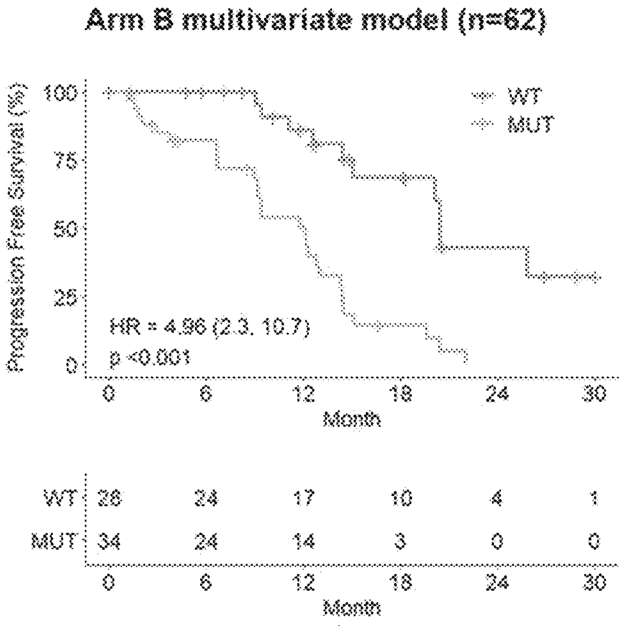

METHOD OF PREDICTING THERAPEUTIC RESPONSE AND PROGNOSIS OF METASTATIC BREAST CANCER TO CHEMOTHERAPEUTIC AGENTS, AND TREATING METASTATIC BREAST CANCER

CROSS-REFERENCE TO RELATED APPLICATIONS

This application is based on and claims priority from Korean Patent Application No. 10-2021-0175108, filed on Dec. 8, 2021, with the Korean Intellectual Property Office, the disclosure of which is incorporated herein in its entirety by reference.

TECHNICAL FIELD

The present disclosure relates to a method of predicting therapeutic response or prognosis of an anticancer drug for metastatic breast cancer, and treating HR+/HER2− metastatic breast cancer.

BACKGROUND

Worldwide, the proportion of premenopausal breast cancer patients out of all breast cancer patients is around 15%, which is very low, but the incidence of premenopausal breast cancer in Korea is much higher than in the West. The proportion of premenopausal breast cancer patients in Korea account for about 50%, and the incidence is high for young patients in their 40s, and patients under the age of 40 account for about 13%, which is twice or more as high as in the West. Domestic and foreign guidelines recommend endocrine therapy as the first-line treatment both before and after menopause, but in Korea, most breast cancer drugs are approved for postmenopausal patients, making it difficult to follow the guidelines. Accordingly, in actual clinical practice, chemotherapy is mainly applied.

Endocrine therapy is recommended in clinical guidelines for both postmenopausal and premenopausal patients in hormone receptor-positive (HR+) and human epidermal growth factor receptor 2-negative (HER2−) metastatic breast cancer (MBC) among breast cancers. Recently, studies have been published showing that a combination of endocrine therapy and cyclin-dependent kinase 4 and 6 (CDK4/6) inhibitors increases clinically significant progression-free survival (PFS) and overall survival (OS). However, in actual clinical practice, a significant number of patients are treated with anticancer chemotherapy when the prognosis is predicted to be poor due to resistance to endocrine therapy or aggressive cancer characteristics and young age. Capecitabine is an anticancer chemotherapy applied to patients with HR+/HER2− metastatic breast cancer, and is one of the most frequently used therapeutic agents. Through prospective studies, the efficacy and safety of capecitabine have been demonstrated through prospective studies. Docetaxel and capecitabine are prescribed together for patients who have failed anticancer chemotherapy with anthracyclines, and capecitabine monotherapy is applied to patients who have failed anticancer chemotherapy with taxanes or anthracyclines. In clinical practice, capecitabine is used as the first chemotherapeutic agent for patients with HR+/HER2− metastatic breast cancer who relapsed during endocrine therapy. In aggressive premenopausal patients with HR+ metastatic breast cancer, capecitabine has a faster therapeutic response than combination therapy of cyclin-dependent kinase 4 and 6 (CDK4/6) inhibitors and endocrine therapy, so it is sometimes advantageous to choose anticancer chemotherapy.

In other words, a significant number of premenopausal patients with HR+/HER2− metastatic breast cancer are being treated with anticancer chemotherapy, and the need for biomarkers capable of predicting therapeutic response accordingly is emerging. However, up to date, there is no commercialized biomarker capable of predicting therapeutic response to anticancer chemotherapy in patients with HR+/HER2− metastatic breast cancer, and it is difficult to predict prognosis using only the existing IHC subtype (ER/PR/HER2 status). Accordingly, the development of new biomarkers and metastatic breast cancer therapeutic methods using the same have been required.

SUMMARY

Under these circumstances, the present inventors conducted research to develop a novel biomarker capable of predicting therapeutic response to anticancer drugs while predicting the prognosis of HR+/HER2− premenopausal metastatic breast cancer, a specific subtype of breast cancer. The present disclosure was completed by collecting and analyzing genetic information and clinical information obtained from breast cancer tissue to discover related gene sets, selecting and combining gene sets suitable for clinical application among the discovered genes, and identifying their usefulness.

Accordingly, an aspect of the present disclosure is to provide a biomarker composition for predicting therapeutic response or prognosis of an anticancer drug for HR+/HER2− metastatic breast cancer.

In addition, another aspect of the present disclosure is to provide a kit for predicting therapeutic response or prognosis of an anticancer drug for HR+/HER2− metastatic breast cancer.

In addition, yet another aspect of the present disclosure is to provide a method of predicting therapeutic response or prognosis of an anticancer drug for HR+/HER2− metastatic breast cancer, and treating HR+/HER2− metastatic breast cancer.

The terms used herein are presented for the description of the specific embodiments but are not intended to limit the present disclosure. The terms in singular form may include plural forms unless otherwise specified. It will be understood that the terms “comprising” or “having,” when used herein, specify the presence of stated features, integers, steps, operations, elements, components, or combinations thereof, but do not preclude the presence or addition of one or more other features, integers, steps, operations, elements, components, and/or combinations thereof in advance.

Unless otherwise defined, all technical and scientific terms used in the embodiments have the same meanings as commonly understood by a skilled expert in the technical field to which the present disclosure belongs. It will be further understood that terms, such as those defined in commonly used dictionaries, should be interpreted as having a meaning that is consistent with their meanings of the context of the relevant art and the present disclosure, and will not be interpreted in an idealized or overly formal sense unless expressly so defined herein.

Hereinafter, the present disclosure will be described in more detail.

According to one aspect of the present disclosure, there is provided a biomarker composition for predicting therapeutic response or prognosis of an anticancer drug for HR (hormone-receptor) positive and HER2 negative (HR+/HER2−) metastatic breast cancer (MBC), in which the composition includes an agent for measuring a mutation existing in one or more types of genes selected from the group consisting of NF2, FAT3, LRP1B, PTEN and RAD50.

In an embodiment of the present disclosure, the composition includes any one or more of NH2 or FAT3; and LRP1B, PTEN, and RAD50. In other words, the biomarker composition may be a combination of 4 or 5 types of genes.

In addition, according to another aspect of the present disclosure, there is provided a method of predicting therapeutic response or prognosis of an anticancer drug for HR (hormone-receptor) positive and HER2 negative (HR+/HER2−) metastatic breast cancer (MBC), and treating HR+/HER2− metastatic breast cancer, in which the method includes: (a) measuring at least one type of mutation selected from the group consisting of NF2, FAT3, LRP1B, PTEN and RAD50 in a biological sample isolated from a subject; (b) comparing the mutation of a gene measured in the sample with a control sample; (c) when the mutation exists, determining that the subject has poor response to a first anticancer drug or poor therapeutic prognosis; and (d) treating the HR+/HER2− metastatic breast cancer by administering an effective amount of a second anticancer drug for breast cancer to the subject determined to have poor response to the first anticancer drug or poor therapeutic prognosis.

In addition, there is provided a method of predicting therapeutic response or prognosis of an anticancer drug for HR (hormone-receptor) positive and HER2 negative (HR+/HER2−) metastatic breast cancer (MBC), and treating HR+/HER2− metastatic breast cancer, in which the method includes: (a) measuring at least one type of mutation selected from the group consisting of NF2, FAT3, LRP1B, PTEN and RAD50 in a biological sample isolated from a subject; (b) comparing the mutation of a gene measured in the sample with a control sample; (c) when the mutation does not exist, determining that the subject has good response to a first anticancer drug or good therapeutic prognosis; and (d) treating the HR+/HER2− metastatic breast cancer by administering an effective amount of the first anticancer drug for breast cancer to the subject determined to have good response to the first anticancer drug or good therapeutic prognosis.

As used herein, the term “subject” refers to a subject whose resistance to a cancer drug is to be identified or predicted. The subject may be a vertebrate, specifically mammals, amphibians, reptiles, birds, etc., and more specifically, mammals, for example, humans (*Homo sapiens*).

As used herein, the term “biological sample” refers to any sample obtained from a target subject in which the expression of the marker gene or protein of an embodiment of the present disclosure may be detected.

Preferably, the biological sample may be at least one selected from the group consisting of saliva, biopsy, blood, serum, plasma, lymph, cerebrospinal fluid, ascites, skin tissue, liquid culture, feces and urine, without being particularly limited thereto, and may be prepared by treatment by a method commonly used in the technical field of the present disclosure.

In the method of an embodiment of the present disclosure, the therapeutic response or prognosis of an anticancer drug for a subject suspected of actual HR+/HER2− metastatic breast cancer may be determined by comparing a mutation in a control group with a mutation in a target subject.

In other words, when mutations are formed (exist) in NF2, FAT3, LRP1B, PTEN, and RAD50 measured from a sample of a target subject compared to the control group, it may be determined that a patient has resistance to a cancer drug. In addition, when the mutation exists in the subject, it may be predicted that the progression-free survival period will be short.

The control group means a subject without a mutation, that is, a wild type or a normal group.

Phase (a) may be a phase of measuring mutations of: any one or more of NH2 or FAT3; and LRP1B, PTEN, and RAD50, but is not limited thereto.

The mutation may be one or more types of variations selected from the group consisting of single nucleotide variation (SNV), insertion/deletion variation (Indel), copy number variation (CNV), deletion and inversion, but is not limited thereto.

The HR+/HER2− metastatic breast cancer may be developed before menopause, but is not limited thereto.

The term “marker” refers to a molecule that is associated quantitatively or qualitatively with the presence of a biological phenomenon. Examples of “markers” include a polynucleotide, such as a gene or gene fragment, RNA or RNA fragment; or a gene product, including a polypeptide such as a peptide, oligopeptide, protein, or protein fragment; or any related metabolites, by products, or any other identifying molecules, such as antibodies or antibody fragments, whether related directly or indirectly to a mechanism underlying the phenomenon. The markers of an embodiment of the present disclosure include the nucleotide sequences (e.g., GenBank sequences) as disclosed herein, in particular, the full-length sequences, any coding sequences, any fragments, or any complements thereof, and any measurable marker thereof as defined above.

As the biomarkers of an embodiment of the present disclosure, “NF2, FAT3, LRP1B, PTEN and RAD50” may use any gene or protein whose sequence information may be found in a known database as long as the aspect of the present disclosure may be achieved. For example, genetic information registered in NCBI may be utilized, but is not limited thereto (for example, NF2 (NM_016418), FAT3 (NM_001008781), LRP1B (NM_018557), PTEN (NM_000314), RAD50 (NM_005732)). In addition, even when some nucleotide sequences or amino acid sequences do not match the mRNA or protein of the gene, a nucleotide sequence or amino acid sequence having a biologically equivalent activity may be regarded as the mRNA or protein of each gene. In addition, mutations may occur in each of the above genes and proteins encoded thereby.

The present inventors first discovered that mutations in NF2, FAT3, LRP1B, PTEN, and RAD50 significantly affected the prognosis of HR (hormone-receptor) positive and HER2 negative (HR+/HER2−) metastatic breast cancer (MBC) and response to specific anticancer drugs.

Accordingly, an embodiment of the present disclosure uses mutations in NF2, FAT3, LRP1B, PTEN, and RAD50 as markers to effectively predict the prognosis of premenopausal HR+/HER2− metastatic breast cancer and its response to specific anticancer drugs, which are distinguished from other types of breast cancer.

The selection and application of these significant markers may determine the reliability of the results. A significant marker may refer to a marker that has high validity because the result obtained from a determination is accurate and high reliability so as to show consistent results even during repeated measurements. The mutations in NF2, FAT3, LRP1B, PTEN and RAD50 as predictive markers for the prognosis and response to specific anticancer drugs were detected only in premenopausal HR+/HER2− metastatic breast cancer. It is a highly reliable marker that is unlikely to be detected in control groups (other types of patients and/or normal subjects). Accordingly, the result determined based on the result obtained by detecting the presence of the biomarker of an embodiment of the present disclosure may be reasonably reliable.

As used herein, the term "prognosis prediction" refers to an act of predicting the course and result of a disease beforehand. More specifically, the course of the disease after treatment may vary depending on the physiological or environmental condition of the patient, and it may be interpreted as meaning all the actions that predict the course of the disease after treatment considering the condition of the patient as a whole.

The term "prognosis" refers to a prediction of disease progression and recovery, and refers to a prospective or preliminary evaluation. According to an aspect of the present disclosure, the term "prognosis" means determining whether treatment success, survival, recurrence, metastasis, drug response, resistance, etc. in a subject after cancer treatment. In other words, the term "prognosis" refers to the expectation on the medical development (e.g., the possibility of long-term survival, the probability of progression-free survival, disease-free survival rate, etc.), includes positive prognosis or negative prognosis, the negative prognosis includes progression of the disease such as recurrence, and drug resistance or mortality, and the positive prognosis includes remission of the disease such as disease-free status, improvement of the disease, or stabilization.

Accordingly, in an embodiment of the present disclosure, prognosis prediction may be interpreted as an act of predicting "progression-free survival (PFS)." The progression-free survival means maintaining a state without recurrence of cancer during or after treatment of a disease. For example, predicting "good prognosis" means that the probability of progression-free survival of a patient is high and the patient maintains a state without recurrence, and predicting "poor prognosis" means that the probability of progression-free survival of a patient is low or short progression-free survival, indicating that the cancer is recurring.

As used herein, the term "prediction of therapeutic response (therapeutic response to anticancer drugs)" refers to predicting whether a patient responds favorably or unfavorably to an therapeutic agent, such as an anticancer drug, or predicting the risk of resistance to an anticancer drug, and predicting the prognosis of the patient after treatment, that is, or progression-free survival. The biomarker for predicting therapeutic response according to an embodiment of the present disclosure may provide information for selecting the most appropriate therapeutic method for a patient with HR+/HER2− metastatic breast cancer.

With respect to the aspects of the present disclosure, the term "prediction of therapeutic response" refers to identifying the presence or characteristics of a disease associated with the expression of the NF2, FAT3, LRP1B, PTEN and RAD50 genes of an embodiment of the present disclosure by measuring the presence or the absence of mutations existing in the genes in a biological sample or tissue sample.

As used herein, the term "anticancer drug-resistance" refers that when a cancer patient is treated with a cancer drug, the drug has no cancer-treating effect from the beginning of the treatment or has cancer-treating effect at the beginning but loses the cancer-treating effect in the course of continuous treatment. For example, in anticancer drug treatment, the general treatment effect may be determined based on the response evaluation criteria of a solid tumor group. According to the criteria, the effect of cancer treatment may be classified into Complete Response (CR), Partial Response (PR), Progressive Disease (PD), or Stable Disease (SD) groups from changes in tumor size.

As used herein, the term "mutation measurement" refers to the presence of a mutation in a gene of NF2, FAT3, LRP1B, PTEN, RAD50 or a combination thereof, or the expression level of the gene. In other words, it may be determined by checking the expression of the mutant protein encoded by the gene.

The agent capable of detecting the mutation means an agent required for amplifying and detecting a mutated gene region, and is a concept including all agents that may be used for gene amplification at the level of a person skilled in the art. For example, it may mean an agent required for polymerase chain reaction (PCR) to detect the mutation. The PCR includes quantitative PCR (qPCR), real-time PCR, Reverse Transcription PCR (RT-PCR), Solid Phase PCR, Competitive PCR, Overlap-extension PCR, Multiplex PCR, Nested PCR, Inverse PCR, Ligation-mediated PCR, ISSR (Intersequence-specific PCR), Methylation-specific PCR (MSP), colony PCR, Miniprimer PCR, Nanoparticle-Assisted PCR (nanoPCR), TAIL-PCR (Thermal asymmetric interlaced PCR), Touchdown (Step-down) PCR, Hot start PCR, In silico PCR, allele-specific PCR, Assembly PCR, asymmetric PCR, Dial-out PCR, Digital PCR (dPCR), or helicase-dependent amplification technology, but is not limited thereto. In addition, the detection of the mutation may utilize a sequencing method known in the art (for example, next generation sequencing (NGS)), but is not limited thereto.

In addition, the agent may be one or more types of genes (mutations) selected from the group consisting of the NF2, FAT3, LRP1B, PTEN, and RAD50, or one or more types selected from the group consisting of a primer, a probe, and an anti-sense nucleotide that specifically binds to its mRNA, without being limited thereto as long as the aspects of the present disclosure may be achieved.

In addition, the agent may be one or more types selected from the group consisting of an oligopeptide, monoclonal antibody, polyclonal antibody, chimeric antibody, ligand, PNA (peptide nucleic acid) and aptamer that specifically bind to one or more types of proteins (mutations) selected from the group consisting of the NF2, FAT3, LRP1B, PTEN, and RAD50, without being limited thereto as long as the aspects of the present disclosure may be achieved.

In an embodiment of the present disclosure, the mutation measurement includes "NF2, FAT3, LRP1B, PTEN and RAD50 mutation detection," which is identifying the presence of a mutation existing in the marker gene of an embodiment of the present disclosure in a biological sample in order to predict the prognosis of HR+/HER2− metastatic breast cancer and predict drug (anticancer drug) response. It may be preferably performed through sequencing.

When the mutation causes a change in mRNA, the presence of the mutation may be determined by measuring the amount of mRNA. Analysis methods therefor include RT-PCR, competitive RT-PCR, real-time RT-PCR, RNase protection assay (RPA), Northern blotting, DNA chips, etc., but are not limited thereto.

In addition, when there is a change in the structure or expression of the protein expressed by the mutation, the presence of the mutant protein may be determined by checking the presence and expression level of the mutant protein. In addition, it is preferable to check the amount of protein using antibodies specifically binding to the protein of the genes. Analysis methods thereof include, but are not limited to, Western blotting, enzyme linked immunosorbent assay (ELISA), radioimmunoassay (RIA), radioimmunodiffusion, Ouchterlony immunodiffusion, rocket immunoelectrophoresis, immunohistostaining, immunoprecipitation assay, complement fixation assay, FACS, and protein chip assay.

As used herein, the term "primer" refers to a strand of short nucleic acid sequences having a free 3'-end hydroxyl group, which may form base pairs with a complementary template and serves as a starting point for replicating a template strand. The primer may start DNA synthesis in the presence of reagents for polymerization (that is, DNA polymerase or reverse transcriptase) and four different nucleoside triphosphates in proper buffer solutions at a proper temperature. In an embodiment of the present disclosure, PCR amplification may be carried out using sense and antisense primers of NF2, FAT3, LRP1B, PTEN and RAD50 mutant polynucleotides so as to predict drug response and/or prognosis of HR+/HER2− metastatic breast cancer based on the production of a desired product. PCR conditions, and the lengths of sense and antisense primers may be appropriately modified based on what is known in the art.

As used herein, the term "probe" refers to a fragment of a nucleic acid such as RNA or DNA corresponding to several to hundreds of bases that may achieve specific binding to DNA or mRNA, and may be labeled to identify the presence of specific DNA or mRNA. Probes may be manufactured in forms of an oligonucleotide probe, a single-stranded DNA probe, a double-stranded DNA probe, an RNA probe, and the like.

In an embodiment of the present disclosure, hybridization may be performed using a probe complementary to the mutant polynucleotides of NF2, FAT3, LRP1B, PTEN and RAD50 of an embodiment of the present disclosure, and the therapeutic response or prognosis of an anticancer drug for HR+/HER2− metastatic breast cancer may be predicted from a hybridization result. Selection of proper probes and hybridization conditions may be modified based on what is known in the art.

The primer or probe of an embodiment of the present disclosure may be chemically synthesized using a phosphoramidite solid scaffold method or other well-known methods. Such nucleic acid sequences may also be modified by various means known in the art. Non-limiting examples of such modifications include methylation, capping, substitution of one or more analogues of natural nucleotides, and nucleotide variation, for example, variation to non-charged linkages (for example: methyl phosphonate, phosphotriester, phosphoroamidate, carbamates, etc.) or charged linkages (for example: phosphorothioate, phosphorodithioate, etc.).

The primer or probe preferably contains 8 or more nucleotides. Hybridization may be achieved by exposing or contacting the primer or probe to the NF2, FAT3, LRP1B, PTEN and RAD50 mutant polynucleotides of an embodiment of the present disclosure. Preferably, these sequences are hybridized with each other under such a proper condition as to minimize non-specific pairings. In the condition suitable for detecting sequences which share 80% to 90% homology, for example, a proper condition may include hybridizing overnight at 42° C. in a buffer containing 0.25 M $Na_2HPO_4$, pH 7.2, 6.5% SDS, and 10% dextran sulfate and finally washing at 55° C. with a solution containing 0.1×SSC and 0.1% SDS. In addition, a condition suitable for detecting a sequence which shares about 90% homology or more may include hybridizing overnight at 65° C. in 0.25M $Na_2HPO_4$, pH 7.2, 6.5% SDS, 10% dextran sulfate, and finally washing at 60° C. with a solution containing 0.1×SSC and 0.1% SDS.

As used herein, the term "antibody" is a term known in the art and refers to a specific protein molecule that indicates an antigenic region. With respect to the aspects of the present disclosure, the antibody binds specifically to the marker of an embodiment of the present disclosure, that is, a polypeptide. This antibody may be produced from a protein which the marker gene cloned typically into an expression vector encodes, using a conventional method. Herein, partial peptides producible from the protein also fall within the scope of the antibody. The partial peptide of an embodiment of the present disclosure is required to contain at least 7 amino acids, preferably 9 amino acids, and more preferably 12 or more amino acids. No particular limitations are imparted to the form of the antibodies of an embodiment of the present disclosure. Among them are polyclonal antibodies, monoclonal antibodies and fragments thereof which contain a paratope, and all immunoglobulin antibodies. Further, special antibodies such as humanized antibodies are also within the antibodies of an embodiment of the present disclosure. Consequently, any antibody against the NF2, FAT3, LRP1B, PTEN and RAD50 mutant proteins of an embodiment of the present disclosure includes all antibodies producible using a method known in the art.

The antibodies used for detection of a marker capable of predicting therapeutic response or prognosis of an anticancer drug for HR+/HER2− metastatic breast cancer of an embodiment of the present disclosure include complete forms having two full-length light chains and two full-length heavy chains, as well as functional fragments of antibody molecules. The functional fragments of antibody molecules refer to fragments retaining at least an antigen-binding function, and include Fab, F(ab'), F(ab')2, Fv, and the like.

According to a preferred embodiment of the present disclosure, the mutation of the marker gene of an embodiment of the present disclosure may be one or more variations selected from the group consisting of a single nucleotide variation (SNV), insertion/deletion variation (Indel), copy number variation (CNV), deletion and inversion.

As used herein, the term "single nucleotide variation (SNV)" refers to a single nucleotide difference in one sequence or in a small number of populations within a species, and mainly refers to a difference from a standard sequence appearing in sequencing data, not that single nucleotide sequence polymorphism refers to a single nucleotide difference in a large number of populations within a species.

As used herein, the term "insertion/deletion variation (Indel)" refers to an insertion or deletion variation that may change the number of nucleic acids in a gene.

As used herein, the term "copy number variation (CNV)" refers to a state in which the copy number of a gene increases or decreases.

The mutation of the gene may include any one or more mutations, and may, for example, have at least one mutation selected from the group consisting of truncating mutation, missense mutation, nonsense mutation, frameshift mutation, in-frame mutation, splice mutation, and splice_region mutation, in addition to the variations described above. The frameshift mutation may be at least one selected from a frameshift insertion (FS ins) mutation and a frameshift deletion (FS del) mutation. The in-frame mutation may be at least one selected from an in-frame insertion (IF ins) mutation and an in-frame deletion (IF del) mutation.

According to a preferred embodiment of the present disclosure, the first anticancer drug (cancer agent or drug) may be any anticancer drug as long as it achieves the aspect of the present disclosure, but is not limited thereto. The first anticancer drug may be capecitabine or 5-fluorouracil, preferably capecitabine, but is not limited thereto. In addition, the second anticancer drug may be different from the first anticancer drug. When a patient with HR+/HER2− metastatic breast cancer is predicted to have low response and poor prognosis to the first anticancer drug, the second anticancer drug having a mechanism different from that of the first anticancer drug may be treated alone or in combination with the first anticancer drug.

For example, when the first anticancer drug is capecitabine or 5-fluorouracil, and the patient's response thereto is low and shows a poor prognosis, a CDK4/6 inhibitor or cytotoxic chemotherapy may be administered as the second anticancer drug, but is not limited thereto.

In an embodiment of the present disclosure, the "CDK4/6 inhibitor" is a substance that inhibits the functions of CDK (cyclin-dependent kinase) 4 and CDK6, and may be used to treat cancer by preventing excessive proliferation of cancer cells. Any CDK4/6 inhibitor may be used, as long as the aspect of the present disclosure is achievable. For example, it may be palbociclib, ribociclib, or abemaciclib, preferably palbociclib, but is not limited thereto.

In an embodiment of the present disclosure, the "cytotoxic chemotherapy" is an anticancer drug that treats cancer by acting on multiple phases by using the property that cancer cells proliferate at a faster rate than normal cells, and thus increase the production of genetic material and protein. Any cytotoxic chemotherapy may be used, as long as the aspect of the present disclosure is achievable. For example, it may be paclitaxel, but is not limited thereto.

When a patient with HR+/HER2− metastatic breast cancer is predicted to have high response and good prognosis for the first anticancer drug, the first anticancer drug may be administered to treat the HR+/HER2− metastatic breast cancer.

According to an example of the present disclosure, the formation (presence) of NF2, FAT3, LRP1B, PTEN and RAD50 mutations in premenopausal HR+/HER2− metastatic breast cancer cells or tissues was found to be correlated with the resistance of a therapeutic agent for premenopausal HR+/HER2− metastatic breast cancer (capecitabine).

For example, in an example of the present disclosure, it was identified that anticancer drug resistance exists and the prognosis is poor when the following mutations exist. More specifically, in the case of NF2, it may include a mutation in which G is changed to A in the nucleotide at position 1400 on the polynucleotide represented by NM_016418; in the case of FAT3, it may include a mutation in which G is changed to A in the nucleotide at position 1067 on the polynucleotide represented by NM_001008781; in the case of LRP1B, it may include a mutation in which C is changed to T in the nucleotide at position 12956 on the polynucleotide represented by NM_018557; in the case of PTEN, it may include a mutation in which T is changed to G in the nucleotide at position 544 on the polynucleotide represented by NM_000314.4; and in the case of RAD50, it may include a mutation in which T is changed to C in the nucleotide at position 353 on the polynucleotide represented by NM_005732. The aforementioned types of mutations are merely examples, but are not limited thereto, and examples of specific mutations identified in the examples of the present disclosure are shown in Table 1. As described above, mutations of NF2, FAT3, LRP1B, PTEN and RAD50 may be used to diagnose resistance to a therapeutic agent for HR+/HER2− metastatic breast cancer and predict prognosis.

In addition, according to another aspect of the present disclosure, there is provided a kit for predicting therapeutic response or prognosis of an anticancer drug for HR+/HER2− metastatic breast cancer, in which the kit includes an agent for measuring one or more types of mutations selected from the group consisting of NF2, FAT3, LRP1B, PTEN, and RAD50.

The kit may be a RT-PCR kit, a microarray chip kit, a protein chip kit, or an NGS kit.

The kit of an embodiment of the present disclosure may detect markers by checking the expression level (presence) of mutant polypeptides of NF2, FAT3, LRP1B, PTEN, and RAD50, which are predictive markers of therapeutic response and prognosis of an anticancer drug, or polynucleotides encoding the same. The kit of an embodiment of the present disclosure may include primers and probes for measuring the expression of the predictive markers of therapeutic response or prognosis of an anticancer drug, or optionally antibodies that recognize markers or fragments thereof that maintain antigen-binding ability, as well as one or more other ingredient compositions or devices suitable for the polypeptide or polynucleotide assay method.

For example, the kit for predicting therapeutic response or prognosis of an anticancer drug for detecting polynucleotides or gene variations of an embodiment of the present disclosure may include one or more types of oligonucleotides that specifically bind to polynucleotides encoding mutant polypeptides of NF2, FAT3, LRP1B, PTEN and RAD50, may include primers corresponding to nucleotides or partial sequences of NF2, FAT3, LRP1B, PTEN and RAD50 mutations, reverse transcriptase, Taq polymerase, primers for PCR and dNTP, and may use a kit using the assay method described in connection with "determination of mRNA expression level" above to measure polynucleotide expression levels.

In addition, the kit of an embodiment of the present disclosure is a kit for predicting therapeutic response or prognosis of an anticancer drug for HR+/HER2− metastatic breast cancer, in which the kit is configured to detect the presence of NF2, FAT3, LRP1B, PTEN and RAD50 mutant proteins, and may include an antibody that specifically binds to NF2, FAT3, LRP1B, PTEN and RAD50 mutant proteins of an embodiment of the present disclosure. In addition, the kit for measuring a protein level may use a kit using the aforementioned method used for "measuring the protein expression level" without limitation. Preferably, the kit may be an ELISA kit or a protein chip kit.

Protein expression using antibodies is measured by forming an antigen-antibody complex between NF2, FAT3, LRP1B, PTEN and RAD50 mutant proteins and their antibodies, and may be quantitatively detected by measuring the amount of formation of the complex by various methods.

As used herein, the term "antigen-antibody complex" refers to binding products of a marker protein to an antibody specific thereto. The amount of formation of the antigen-antibody complex may be quantitatively determined by measuring the signal intensity of a detection label.

In addition, the kit of an embodiment of the present disclosure may include an antibody that specifically binds to a marker component, a secondary antibody conjugate conjugated with a label that develops color by reaction with a substrate, a color-developing substrate solution that will color react with the label, a washing solution and an enzyme reaction stop solution, and may be manufactured in a number of separate packaging or compartments containing reagent components to be used.

Since the method of an embodiment of the present disclosure uses the above-described mutation detection method, the description of the contents overlapping therewith is omitted in order to avoid the excessive complexity of the present specification.

When the biomarker of an embodiment of the present disclosure is used as a marker for predicting therapeutic response or prognosis of an anticancer drug for metastatic breast cancer of a specific type, it is possible to predict therapeutic response or prognosis of an anticancer drug, and accordingly, a therapeutic method suitable for a patient may be applied to maximize the treatment effect.

BRIEF DESCRIPTION OF THE DRAWINGS

FIG. 1 shows the results according to a combination of five selected biomarker genes associated with drug therapeutic response and prognosis of premenopausal HR+/HER2− metastatic breast cancer.

FIG. 2 is a PFS analysis result using IHC classification.

FIG. 3 is a PFS analysis result using five types of marker combinations selected in an embodiment of the present disclosure.

DETAILED DESCRIPTION

Hereinafter, the examples are only for explaining the present disclosure in more detail, and it will be apparent to those skilled in the art to which the present disclosure pertains that the scope of the present disclosure is not to be construed as being limited by these examples according to the gist of the present disclosure.

Example 1. Selection of Biomarker Genes Associated with Drug Therapeutic Response and Prognosis of Premenopausal HR+/HER2− Metastatic Breast Cancer The present inventors attempted to discover biomarkers capable of predicting therapeutic response and prognosis of a specific drug for patients with premenopausal HR+/HER2− [HR (hormone-receptor)-positive and HER2− negative] metastatic breast cancer (MBC), who exhibited different therapeutic methods (response) and prognosis than early breast cancer patients.

In this regard, through the next generation sequencing (NGS, DNA/RNA) of patients treated with capecitabine (Xeloda®), a specific gene mutation associated with the survival of breast cancer patients, and CNV (gene copy number variation) were identified. In addition, a model was constructed through survival analysis after combining the follow-up survival data of the patients who received the drug (Median follow-up=17.7 months) with the NGS results.

The target patients from whom the breast cancer samples were collected agreed to the use of the clinical sample tissues for the purpose of the study according to an embodiment of the present disclosure, and the histologic classification and tumor stage of the target patients from whom the breast cancer samples were collected were reviewed by a pathologist.

More details follow:

Among 141 premenopausal HR+/HER2− MBC patients, a tumor sample was isolated from a group (n=62) administered with capecitabine, and sequencing was performed on the sample. CancerSCAN™ targeted panel sequencing was performed to detect 375 cancer-related gene variations, and transcriptome analysis was performed to detect overall gene expression patterns. Genomic differences related to drug response in PFS in patients with poor prognosis and patients with good prognosis using gene variation and gene expression were examined.

A univariate Cox proportional hazard model was analyzed for each genetic variation/CNV, the p-value derived by the log-rank test was defined as a p-value cutoff of 0.05 as the criterion for a statistically significant difference, and 30 biomarkers with p-value<0.05 were selected as candidate markers. Based thereon, the final five genes, in other words, NF2 (moesin-ezrin-radixin like (MERLIN) tumor suppressor), FAT3 (FAT atypical cadherin 3), LRP1B (LDL receptor related protein 1B), PTEN (phosphatase and tensin homolog) and RAD50 (RAD50 double strand break repair protein), were derived as biomarkers through the stepwise variable selection process of multivariate Cox proportional hazard model analysis. Among them, in the case of the NF2 and FAT3 genes included in the Hippo pathway gene, the number of individuals with mutations is small and these genes belong to the gene group that performs the same function in relation to the Hippo pathway. Hence, survival analysis was performed by bundling the two genes and considering them as one marker. In other words, the description of "NF2+FAT3" includes the case where there exists a mutation in either NF2 or FAT3 gene.

The multivariate Cox proportional model analysis results integrating all of the aforementioned gene mutations are shown in FIG. 1.

As shown in FIG. 1, when FAT3+NF2 mutation (35.5%), LRP1B mutation (14.5%), PTEN mutation (4.8%), and RAD50 mutation (12.9%) exist in young premenopausal metastatic breast cancer patients of HR+/HER2−[HR (hormone-receptor)-positive and HER2-negative], the prognosis was found to be poor.

In other words, generic modifications such as NF2 mutation, FAT3 mutation, LRP1B mutation, PTEN mutation, and RAD50 mutation found in the HR+/HER2− premenopausal MBC group were significantly associated with progression-free survival (PFS) and capecitabine resistance in patients.

In addition, the results of analyzing the ratio of patients with mutations among patients used in this analysis and the ratio of patients with corresponding mutations among normal people are shown in Table 1, and the types of mutations possessed by patients used in this analysis are shown in Table 2.

TABLE 1

| Gene | YoungPEARL_Capecitabine | 1000Genome |
|---|---|---|
| NF2 | 2% | 0% |
| FAT3 | 34% | 2% |
| LRP1B | 15% | 0% |
| PTEN | 5% | 0% |
| RAD50 | 13% | 0% |

In Table 1, 1000Genome is a database that analyzes the mutation frequency of normal population (internationalgenome.org). It was identified that normal people possess no mutation in the gene selected in an embodiment of the present disclosure or possess only a very low ratio.

TABLE 2

| | Gene | RefseqID | cDNA | cDNA pos | Ref | Alt | AAchange | Func | Genomic position | n.pt |
|---|---|---|---|---|---|---|---|---|---|---|
| 1 | PTEN | NM_000314 | c.5445>G | 544 | T | G | L182V | nonsynonymous SNV | chr10: g89711926T>G | 1 |
| 2 | PTEN | NM_000314 | c.5445>G | 556 | C | G | L186V | nonsynonymous SNV | chr10: g89711938C>G | 1 |
| 3 | PTEN | NM_000314 | c.635-1G>A | 635 | G | A | — | splicing | chr10: g89717609G>A | 1 |
| 4 | PTEN | NM_000314 | c.672A>G | 672 | A | G | I224M | nonsynonymous SNV | chr10: g89717647A>G | 1 |
| 5 | PTEN | NM_000314 | c.950_953delTACT | 950_953 | TACT | — | p.VL317fs | frame shift deletion | chr10: g89720799TACT>- | 1 |
| 6 | FAT3 | NM_001008781 | c.1067G>A | 1067 | G | A | C356Y | nonsynonymous SNV | chr11: g92086345G>A | 1 |
| 7 | FAT3 | NM_001008781 | c.1810G>A | 1810 | G | A | D604N | nonsynonymous SNV | chr11: g92087088G>A | 1 |
| 8 | FAT3 | NM_001008781 | c.2309C>T | 2309 | C | T | T770M | nonsynonymous SNV | chr11: g92087587C>T | 1 |
| 9 | FAT3 | NM_001008781 | c.3872A>G | 3827 | A | G | Y1276C | nonsynonymous SNV | chr11: g92495179A>G | 1 |
| 10 | FAT3 | NM_001008781 | c.5599G>A | 5599 | G | A | V1867I | nonsynonymous SNV | chr11: g92531778G>A | 1 |
| 11 | FAT3 | NM_001008781 | c.6173G>A | 6173 | G | A | R2058H | nonsynonymous SNV | chr11: g92532352G>A | 1 |
| 12 | FAT3 | NM_001008781 | c.6378C>A | 6378 | C | A | D2126E | nonsynonymous SNV | chr11: g92532557C>A | 1 |
| 13 | FAT3 | NM_001008781 | c.6823T>G | 6823 | T | G | L2275V | nonsynonymous SNV | chr11: g92533002T>G | 1 |
| 14 | FAT3 | NM_001008781 | c.8047G>A | 8047 | G | A | G2683R | nonsynonymous SNV | chr11: g92534226G>A | 1 |
| 15 | FAT3 | NM_001008781 | c.8200C>T | 8200 | C | T | P2734S | nonsynonymous SNV | chr11: g92534379C>T | 1 |
| 16 | FAT3 | NM_001008781 | c.8942A>C | 8942 | A | C | E2981A | nonsynonymous SNV | chr11: g92538364A>C | 1 |
| 17 | FAT3 | NM_001008781 | c.9877A>G | 9877 | A | G | I3293V | nonsynonymous SNV | chr11: g9268041A>G | 2 |
| 18 | FAT3 | NM_001008781 | c.19976A>G | 9976 | A | G | T3326A | nonsynonymous SNV | chr11: g92568140A>G | 1 |
| 19 | FAT3 | NM_001008781 | c.10124A>G | 10124 | A | G | Q3375R | nonsynonymous SNV | chr11: g92569769A>G | 1 |
| 20 | FAT3 | NM_001008781 | c.11020C>T | 11020 | C | T | R3674W | nonsynonymous SNV | chr11: g92577553C>T | 4 |
| 21 | FAT3 | NM_001008781 | c.11039A>T | 11039 | A | T | Q3680L | nonsynonymous SNV | chr11: g92577572A>T | 1 |
| 22 | FAT3 | NM_001008781 | c.11491G>C | 11491 | G | C | E3831Q | nonsynonymous SNV | chr11: g92590505G>C | 1 |
| 23 | FAT3 | NM_001008781 | c.12412G>A | 12412 | G | A | V4138M | nonsynonymous SNV | chr11: g92616034G>A | 1 |
| 24 | FAT3 | NM_001008781 | c.12763G>A | 12763 | G | A | G4255R | nonsynonymous SNV | chr11: g92616385G>A | 1 |
| 25 | FAT3 | NM_001008781 | c.13271C>T | 13271 | C | T | P4424L | nonsynonymous SNV | chr11: g92623876C>T | 1 |
| 26 | FAT3 | NM_001008781 | c.13549G>A | 13549 | G | A | V4517M | nonsynonymous SNV | chr11: g92624154G>A | 1 |
| 27 | LRP1B | NM_018557 | c.12956G>A | 12956 | C | T | R4319K | nonsynonymous SNV | chr2: g141055388C>T | 1 |
| 28 | LRP1B | NM_018557 | c.11483G>T | 11483 | C | A | R3828L | nonsynonymous SNV | chr2: g141113958C>A | 2 |
| 29 | LRP1B | NM_018557 | c.7045C>G | 7045 | G | C | L2349V | nonsynonymous SNV | chr2: g141356349G>C | 1 |
| 30 | LRP1B | NM_018557 | c.6493C>T | 6493 | G | A | R2165W | nonsynonymous SNV | chr2: g141458125G>A | 1 |
| 31 | LRP1B | NM_018557 | c.6355A>G | 6355 | T | C | T2119A | nonsynonymous SNV | chr2: g141459362T>C | 1 |
| 32 | LRP1B | NM_018557 | c.5734G>A | 5734 | C | T | A1912T | nonsynonymous SNV | chr2: g141526806C>T | 1 |
| 33 | LRP1B | NM_018557 | c.4697A>G | 4697 | T | C | K1566R | nonsynonymous SNV | chr2: g141609235T>C | 1 |
| 34 | LRP1B | NM_018557 | c.3766G>A | 3766 | C | T | D1256N | nonsynonymous SNV | chr2: g141660489C>T | 1 |
| 35 | NF2 | NM_015418 | c.1400G>A | 1400 | G | A | R467K | nonsynonymous SNV | chr22: g30070884G>A | 1 |
| 36 | RAD50 | NM_005732 | c.353T>C | 353 | T | C | I118T | nonsynonymous SNV | chr5: g131911608T>C | 1 |
| 37 | RAD50 | NM_005732 | c.1102G>A | 1102 | A | A | D368N | nonsynonymous SNV | chr5: g131924429G>A | 1 |
| 38 | RAD50 | NM_005732 | c.1211A>G | 1211 | A | G | Q404R | nonsynonymous SNV | chr5: g131924538A>G | 3 |
| 39 | RAD50 | NM_005732 | c.1456C>T | 1456 | C | T | R486C | nonsynonymous SNV | chr5: g13196919C>T | 1 |
| 40 | RAD50 | NM_005732 | c.2603A>G | 2603 | A | G | N868S | nonsynonymous SNV | chr5: g131940576A>G | 1 |
| 41 | RAD50 | NM_005732 | c.3790C>T | 3790 | C | T | L1264F | nonsynonymous SNV | chr5: g131977907C>T | 1 |

Example 2. Verification of Selected Biomarker Genes Related to Drug Therapeutic Response and Prognosis of Premenopausal HR+/HER2− Metastatic Breast Cancer As identified in Example 1, in order to prove that five types of marker combinations associated with NF2 mutation, FAT3 mutation, LRP1B mutation, PTEN mutation, and RAD50 mutation, may be applied as an important indicator for determining the prognosis of premenopausal HR+/HER2− metastatic breast cancer and/or response to capecitabine, the present inventors performed a PFS analysis using the existing IHC model, and performed a comparative analysis to see if it had a significant result in predicting prognosis.

First, Cox proportional hazards analysis was used to identify statistical significance whether it is more significant than the clinical information-based prognostic evaluation model. For clinical information using IHC classification, individual markers, and each of the five types of marker combinations selected in Example 1, the performance of the predictive model was calculated by C-index and compared. In general, when the C-index is greater than 0.7, it may be determined that the diagnostic marker performance evaluation index, AUC, corresponds to a value greater than 0.7, and that the performance of the predictive model is acceptable. The results are shown in Table 3.

TABLE 3

| | | C-index (Cox model performance) | |
|---|---|---|---|
| Variable type | Variable list | Univiariate | Multivariate |
| Clinical variable | IHC.type | 0.514 (0.44, 0.589) | |
| Genomic variable | FAT3 + NF2 | 0.577 (0.489, 0.665) | |
| | LRP1B | 0.583 (0.515, 0.65) | |
| | PTEN | 0.537 (0.485, 0.59) | |
| | RAD50 | 0.584 (0.518, 0.65) | |
| | FAT3 + NF2, LRP1B, PTEN, RAD50 | | 0.737 (0.665, 0.81) |

As shown in Table 3, the C-index was 0.514 in the group using IHC type, which is clinical information, and 0.537 to 0.584 for individual markers, making it difficult to say that the performance of the predictive model was excellent. In the group using five types of marker combinations according to an embodiment of the present disclosure, the C-index value was identified to be 0.737, which identified that it had acceptable discrimination performance.

In addition, the results of PFS analysis using clinical information using IHC classification and five types of marker combinations selected in Example 1 are shown in FIGS. 2 and 3 by applying Kaplan Meier analysis.

As shown in FIG. 2, in the case of using the IHC classification, it was not possible to identify a significant difference in PFS according to each group, and it was identified that the prognosis analysis was impossible accordingly.

However, as shown in FIG. 3, as a result of comparative analysis of patients in whom mutations were not detected for all of the five genes as WT (normal group) and the mutant group, when the marker combination according to an embodiment of the present disclosure was used, it was identified that the mutant group had a relatively poor prognosis as the risk was about 5 times higher than that of the normal group and the median PFS was short at 12 months.

Accordingly, through the above analysis results, it was identified that in the case of using the biomarker set selected in an embodiment of the present disclosure, it was possible to predict drug therapeutic response and prognosis of premenopausal HR+/HER2− metastatic breast cancer, through which the selection of a therapeutic method was able to be optimized and the therapeutic effect was able to be increased.

Although the present disclosure has been described in detail with reference to the specific features, it will be apparent to those skilled in the art that this description is only for a preferred embodiment and does not limit the scope of the present disclosure. Thus, the substantial scope of the present disclosure will be defined by the appended claims and equivalents thereof.

What is claimed is:

1. A method of treating hormone-receptor positive and HER2 negative (HR+/HER2−) metastatic breast cancer in a premenopausal subject, the method comprising:

(a) detecting, in a biological sample obtained from the subject, whether a combination of mutations is present, wherein the combination comprises: (i) a mutation in NF2 or FAT3, (ii) a mutation in LRP1B, (iii) a mutation in PTEN, and (iv) a mutation in RAD50; and (b) administering to the subject a therapeutically effective amount of a first anticancer drug when the combination of mutations is not present, or administering to the subject a therapeutically effective amount of a second anticancer drug when the combination of mutations is present, wherein the first anticancer drug is capecitabine or 5-fluorouracil, and wherein the second anticancer drug is different from the first anticancer drug.

2. The method of claim 1, wherein the biological sample is at least one selected from the group consisting of saliva, biopsy, blood, serum, plasma, lymph, cerebrospinal fluid, ascites, skin tissue, liquid culture, feces and urine.

3. The method of claim 1, wherein each mutation of the combination is one or more types of variations selected from the group consisting of single nucleotide variation (SNV), insertion/deletion variation (Indel), copy number variation (CNV), deletion and inversion.

4. The method of claim 1, wherein the second anticancer drug is a CDK4/6 inhibitor or cytotoxic chemotherapy.

5. The method of claim 4, wherein the CDK4/6 inhibitor is palbociclib.

6. The method of claim 4, wherein the cytotoxic chemotherapy is paclitaxel.

* * * * *